United States Patent [19]

Diamond

[11] 4,311,141

[45] Jan. 19, 1982

[54] BREAST PUMP

[76] Inventor: Arthur D. Diamond, 7511 Venetian St., #1, Miramar, Fla. 33023

[21] Appl. No.: 130,023

[22] Filed: Mar. 13, 1980

[51] Int. Cl.³ ............................................. A61M 1/06
[52] U.S. Cl. .................................. 128/281; 128/278; 128/300
[58] Field of Search ........................ 141/65; 417/469; 119/14.25, 14.26, 14.42; 128/276, 277, 278, 280, 281, 298, 299, 300, 218 P, 273, 297; 92/117 R, 165 PR, 165 R

[56] References Cited

U.S. PATENT DOCUMENTS

| | | | |
|---|---|---|---|
| 657,440 | 9/1900 | McCaw | 128/278 |
| 714,738 | 12/1902 | Perry | 128/278 |
| 790,051 | 5/1905 | Halstead | 128/281 |
| 2,049,872 | 8/1936 | Sera | 141/65 |
| 2,419,795 | 4/1947 | Saunders | 128/297 |
| 3,881,484 | 5/1975 | Gidcumb, Jr. | 128/218 P |
| 4,278,089 | 7/1981 | Huck et al. | 128/278 |

FOREIGN PATENT DOCUMENTS 678407 12/1929 France ............................... 128/281

*Primary Examiner*—Robert W. Michell
*Assistant Examiner*—J. Kruter
*Attorney, Agent, or Firm*—John Cyril Malloy

[57] ABSTRACT

A breast pump for manually sucking milk from a breast. The pump includes two portions, a first closed top and open bottom portion with the top having an opening and a second portion being open top and closed bottom with a side wall having an opening. A breast shield comprising a funnel-like member for fitting over a breast and a tubular member extending through the top opening of the first member, the tubular member having a predetermined length and extending into the second open-ended portion and including a valve means opening when the portions are pulled apart and closing when the portions are pushed together; the second portion including conduit means connected to the opening in the side wall, the conduit means include valve means closing when the portions are pulled apart and opening when the portions are pushed together, thereby when the elements described above are connected in hooked-up sliding engagement, the liquid extracted may flow through the portions and out the conduit means. Means are provided for keying sliding movement of the portions.

9 Claims, 2 Drawing Figures

BREAST PUMP

BACKGROUND OF THE INVENTION

TECHNICAL FIELD OF THE INVENTION

This invention relates to manually operated pumps and more particularly to a pump designed to extract liquid from a breast.

Recent reports have shown breast feeding of infants to be more desirable over prepared formula feeding. The reports have further shown that an infant nursed with the mother's natural unadulterated milk may have a better chance at a happier more peaceful existence.

In this light, many mothers have started returning to a policy of feeding their children their own milk. As is perhaps well known, a child does not always desire to be fed at a convenient time or place. Oftentimes, a mother works or is otherwise separated from her child, whether voluntarily, as when she goes out for an evening, or involuntarily, as by a sickness, yet, by using the invention the child may still have the full benefit of the mother's nourishing milk. Also, when a mother is in a public place with her infant child, the infant may desire to be fed at that moment; and, if the mother does not want to expose her breast at a particular time or place, she may, nevertheless, carry a convenient supply of her own milk for the child instead of being forced to feed the infant a prepared formula, let the infant cry, or seek a semi-private place. Since none of these latter alternatives is satisfactory, it is apparent that there is a need for the instant invention to be described more fully hereinafter.

It is under these circumstances the applicant has developed his invention, a mechanical device capable of extracting milk from a mother's breast and after extraction storing it in a receptacle for use in a public or a convenient place without the risk of the mother having to expose her breasts or other undesirable circumstances as described above.

The device is relatively simple as is explained more fully hereinafter.

SUMMARY OF THE INVENTION

The invention comprises a pump consisting of a first open-ended cylinder portion, having a closed top end, with a hole therein and centrally located therein, and a second portion keyed for sliding movement with the first portion, having an open end confronting the first portions open end, and a closed bottom end with a hole in the side wall. A breast shield having a front funnel open portion and a second bottom tubular portion extends through the top closed first portion member into the second open-ended second portion member, wherein fluid may flow from the open funnel portion down through the tubular portion and collect in the second open-ended portion when the pump portions are slidably moved creating a vacuum in the first portion. A washer is inserted between the first member and second member creating a sealed off first member open portion. When the pump portions are pushed together in a slidable manner a valve means in the tubular member closes and a conduit member connected to the hole in the side wall, including a conduit means having a valve member which opens when the members are split together allows the milk to flow from the funnel to the conduit means, through the pump and into a receptacle.

In accordance with these and other objects of the invention which will become apparent hereinafter, the invention will now be described with reference to the accompanying drawings in which:

DESCRIPTION OF THE PREFERRED EMBODIMENT

Figure 1:
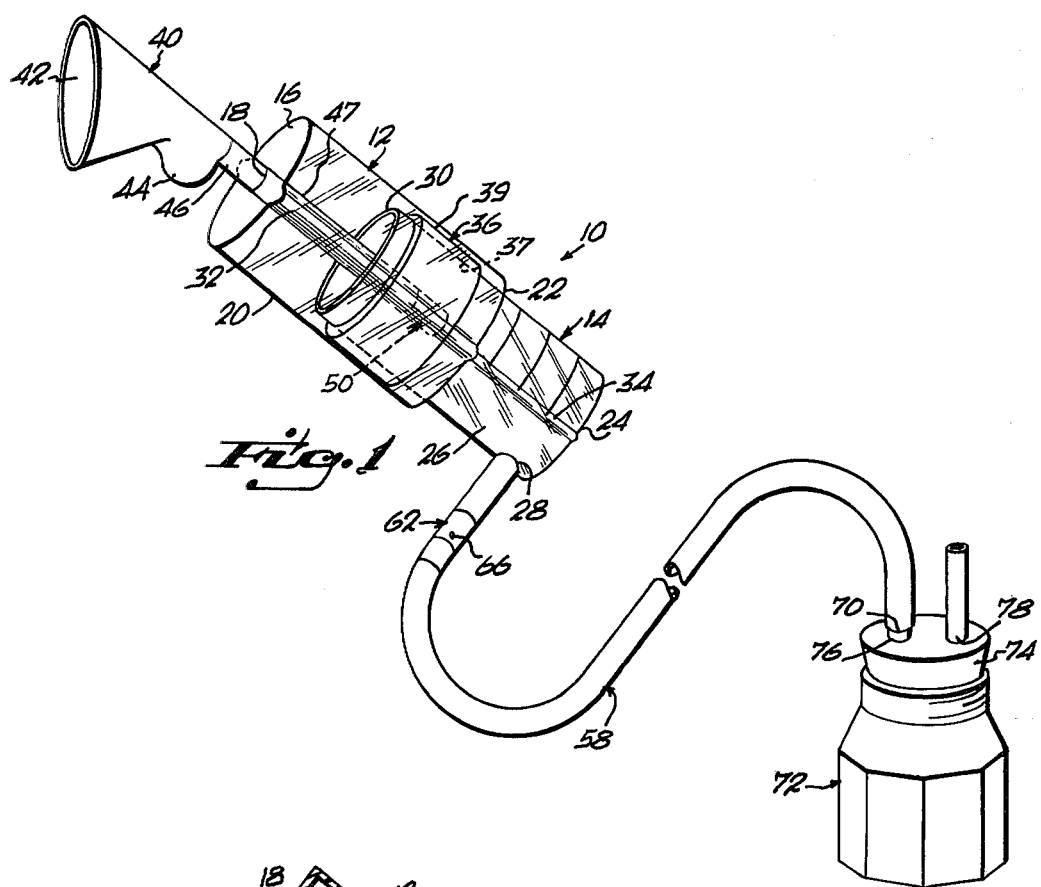
FIG. 1 is a perspective view of the invention, a breast pump showing the elements adapted for operational engagement.

Referring to the drawings wherein like reference characters designate like or corresponding parts throughout the several views and referring particularly to FIG. 1, there is shown the invention, a breast pump, generally denoted by the numeral 10. As can be seen from FIG. 1, the pump comprises a first portion 12 and a second portion 14. The first portion is generally cylindrical having a closed top end 16 with an opening 18, side walls 20, and an open bottom end 22. The second portion 14 includes a bottom end 24, side walls 26. The side walls having an opening at 28. The second portion includes an open upper end 30 adapted for sliding engagement within first portion 12.

Figure 2:
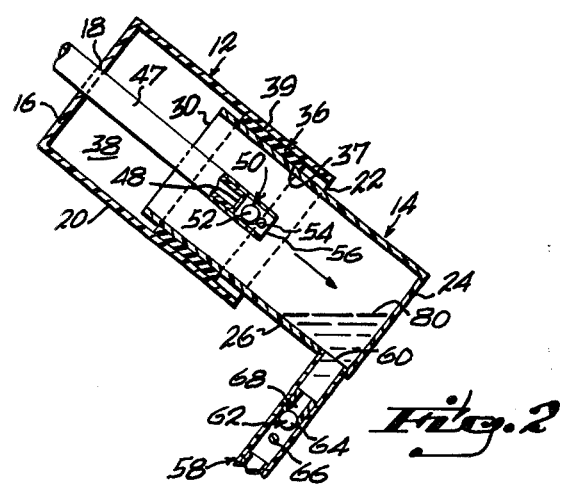
FIG. 2 is a cross sectional plan view of the breast pump shown in FIG. 1.

As can be seen from FIGS. 1 and 2, the members have a predetermined diameter with the first portion having a greater diameter than the second portion.

The portions 12 and 14 are keyed for sliding engagement with one another through a keying means comprising an outwardly extending flange 32 of the first portion and 34 of the second portion. The second portion flange 34 is smaller in dimension than the first portion flange 32 for compatibly sliding engagement of the portions.

The pump includes a gasket member 36 interposed between the first portion 12 and the second portion 14, as can be clearly seen in FIG. 2. The gasket 36 includes an inside surface 37 abutting the first portion and an outside surface 39 abutting the second portion, thereby sealing off the space generally designated 38, which becomes a vacuum as will be more fully appreciated hereinafter.

The breast pump includes a breast shield 40 having a first opening 42 sized to compatibly mate with and comfortably fit over a breast. The shield may include a middle portion 44 made of a flexible material being located toward the lower gravitational end of the shield for preventing dripping and generally serving as an anti-drip means as will be appreciated more fully hereinafter. The shield includes a lower portion 46 comprising a tubular member 47 having a terminal end 48 including valve means 50 located downwardly from the breast shield and extending into the second portion 14.

The valve means 50 comprises a conventional ball valve means including a ball 52 and a keeper pin 54, with an open terminal end 56. As will be readily appreciated by one skilled in the art, the ball is free to move from the opening 48 to the pin 46, depending on the pressure surrounding the ball.

The pump includes a conduit means generally denoted 58 in FIG. 1 and as seen with more particularity in FIG. 2. The conduit means includes a first open end 60, a valve means 62 at opening 60 comprising a ball 64 and a pin 66, wherein the ball 64 may move to and from the abutting wall structure 68 and pin 66 as is ordinary in the case of such ball valves.

When fluid is allowed to be passed through the ball valve 62, it flows through the conduit 58 to a terminal open end 70 adapted for connection with a receptacle, such as that shown in FIG. 1 and denoted generally by 72.

It has been found that the optimum receptacle is a receptacle comprising a stopper such as 74 having two openings such as 76 and 78 with tubular members extending therefrom to promote the extraction of milk from the breast.

IN USE

In use, the device is adapted to have the shield 40 compatibly mated with a breast and it has been found that the dimension of the opening 42 should be between 2½ and 3 inches, depending on the size of the breast. When the portions of the pump 12 and 14 are pulled apart, the valve 50 opens so that the ball 52 moves against the keeper pin 54, allowing fluid to be drawn from the breast and collect in the second portion 14 in the space generally denoted by the numeral 80. When the portions are pushed together, the second valve 62 opens with the ball 64 moving against pin 66, allowing fluid to flow from the collection point, generally denoted 80 through the conduit means 58 to a terminal open end 70 and to receptacle 72 of FIG. 2.

In this way, the mother's milk can be collected in a receptacle such as 72 for feeding at a convenient time. Thus, the mother can in effect breast feed her child in public without exposing her private parts. Further, the mother does not have to sacrifice feeding her child the preferred natural milk, avoiding the inconvenience and perhaps dilatorious effects of feeding the child a prepared formula.

While the description and disclosure accompanying the same have been described herein in what is conceived to be the most practical and preferred embodiment, it is recognized that departures may be made therefrom, such as by deleting the tube and filling the bottle directly using the device, within the scope of the invention, which is therefore not to be limited to the details disclosed herein but is to be accorded the full scope of the claims so as to embrace any and all equivalent apparatus and articles.

What is claimed:

1. A breast pump for manually extracting milk from a breast comprising:

a pump comprising;

a first generally cylindrical portion having a first diameter including an open bottom end and a top end having an opening, a second generally cylindrical portion having a second diameter having a closed bottom end and open top end and annular side walls having a single opening, the portions having predetermined diameters, the first diameter being greater than the second, and a gasket member having an inside surface adapted for tight abutting engagement with the second portion and an outside surface adapted for loose abutting engagement with the first portion, and flanged means for keying the first and second portion for sliding longitudinal movement and to prevent transverse rotation, a breast shield including a first funnel-like opening, a middle portion and a lower second portion comprising a tubular downwardly extending member having a terminal end including a first valve means extending into the second portion when the first and second portions are in sliding engagement, engagement means to connect the breast shield tubular member with the first member top opening, means adapting the second portion for receiving conduit means at its side wall opening, the conduit means including a first portion adjacent the second portion side walls having second valve means and a second terminal portion including an open end adapted for fitting to a receptacle, the first valve means opening when the portions are pulled apart to form a partial vacuum and closing when the portions are pushed together, and the second valve means closing when the portions are pulled apart and opening when the portions are pushed together.

2. The device as set forth in claim 1 wherein the portions are keyed for sliding movement with the gasket member inserted inbetween, the breast shield is inserted with its tubular member extending from the first portion opening, the conduit means connected to the second portion side wall opening and a receptacle for storage of liquid is connected to the terminal end of the conduit means.

3. The device set forth in claim 1 wherein the collector receptacle includes a top end comprising a stopper having two openings, a first opening connected to the conduit means terminal end and a second opening having a tubular member.

4. The device set forth in claim 3, wherein the funnel member includes a middle flexible enlarged portion defining an anti-drip means.

5. The device set forth in claim 4, wherein the funnel has a predetermined diameter of between 2½ and 3 inches.

6. The device set forth in preceding claim 5 wherein the first portion side walls and second portion side walls have a predetermined common length.

7. The device set forth in claim 6 wherein the diameter of the first portion equals 3 inches.

8. The device set forth in claim 7 first and second portions side walls have a common length of 5 inches.

9. The device set forth in claim 2, wherein the first and second valve means comprise ball valve means including a ball and a keeper pin.

* * * * *